(12) United States Patent
Schmid et al.

(10) Patent No.: US 7,070,815 B2
(45) Date of Patent: Jul. 4, 2006

(54) ANTI DIARRHOEA COMPOSITIONS

(75) Inventors: Ulrike Schmid, Wormerveer (NL); Wiro Stam, Wormerveer (NL); Geoff Collins, Wormerveer (NL); Johan Verhaart, Wormerveer (NL)

(73) Assignee: Loders Croklaan USA LLC, Channahon, IL (US)

( * ) Notice: Subject to any disclaimer, the term of this patent is extended or adjusted under 35 U.S.C. 154(b) by 0 days.

(21) Appl. No.: 10/717,903

(22) Filed: Nov. 21, 2003

(65) Prior Publication Data

US 2004/0131712 A1     Jul. 8, 2004

(30) Foreign Application Priority Data

Nov. 27, 2002   (EP) .................................. 02080021

(51) Int. Cl.
*A61K 35/78* (2006.01)

(52) U.S. Cl. ........................ 424/725; 424/439; 424/442

(58) Field of Classification Search ................ 424/725, 424/439, 442
See application file for complete search history.

(56) References Cited

U.S. PATENT DOCUMENTS 6,149,961 A * 11/2000 Kepplinger et al. ........ 426/553

FOREIGN PATENT DOCUMENTS

| EP | 1 001 007 A1 | 5/2000 |
| GB | 932662 | 7/1963 |
| GB | 2 134 767 A | 8/1984 |
| WO | WO 01/03712 A1 | 1/2001 |
| WO | WO 01/05245 A1 | 1/2001 |
| WO | WO 02/055087 A1 | 7/2002 |
| WO | WO 02/056879 A1 | 7/2002 |

OTHER PUBLICATIONS http://digestive.niddk.nih.gov/ddisease/pubs/diarrhea/.*
Goyal, et al., Bangladesh J. Sci. Ind. Res, XXII (1-4):68-71 (1987).

* cited by examiner

*Primary Examiner*—Susan D. Coe
(74) *Attorney, Agent, or Firm*—Morgan Lewis & Bockius LLP

(57) ABSTRACT

The invention concerns a method for the prevention/curing/treatment of diarrhoea in mammals by administering the mammals an effective daily amount of a composition comprising as active component(s) phytosterols and/or pentacyclotriterpenes as present in or derived from Shea oil as well as a method for the preparation of a food or a feed product comprising carbohydrates and proteins wherein the food or feed product has anti-diarrhoea or anti scouring properties by the incorporation of an effective amount of phytosterols and/or pentacyclotriterpenes as present in or derived from Shea oil as active component.

12 Claims, 1 Drawing Sheet

ANTI DIARRHOEA COMPOSITIONS

In a number of areas such as in the pig breeding area but also in the medical area for humans, in particular for babies a known problem with the young mammals is that they easily suffer from diarrhoea. In the breeding industry an attempt to try to prevent and/or treat and/or cure diarrhoea (also named scour in the cattle industry) in the mammals sensitive for or suffering from it use was made of so called antimicrobial growth promoters (=AMGP's). Although some of these AMGP's give some relief they also possess a number of disadvantages such as that their use leads to the development of a resistance of the bacterial colonies responsible for the diarrhoea against the AMGP's. Therefore a number of National Health Organisations already decided that within a short period from now the use of these AMGP's will be prohibited. This created a great need to find replacers that are at least as effective as the AMGP's used so far, but for which the bacteria have not developed a resistance.

As the problems with diarrhoea are the most severe with weaning piglets and with babies the replacers should also be safe to use for these groups of mammals.

According to WO 02/056879 natural terpenes wherein the building block is a hydrocarbon isoprene can be used for this purpose. However, these compounds have a number of disadvantages such as that they do not seem to reduce the incidence of number of veterinary control that is necessary for the young mammals fed with such components.

We studied whether we could find a useful replacer for the known AMGP's that are safe to use both for babies and for weaning piglets but also for other young mammals. Further these compounds should be effective and should not lead to a resistance within the bacteria responsible for the diarrhoea. Moreover these replacers should not have a negative effect on the growth (weight increase) of the young mammals when using them. Another requisite of these replacers being that they should not increase the incidence of number of veterinary controls necessary for the young mammals using the replacer during the weaning period.

The above studied has resulted in our novel invention. This invention concerns in the first instance a method for the prevention/curing/treatment of diarrhoea in mammals by administering the mammals an effective daily amount of a composition comprising as active component(s) phytosterols and/or pentacyclotriterpenes as present in shea oil or in fractions thereof. Preferably the young mammals are weaning piglets or babies.

The invention also provides the use of composition comprising as active component(s) phytosterols and/or pentacyclotriterpenes as present in or derived from Shea oil in the manufacture of an agent for the prevention and/or treatment of diarrhoea. Suitable agents include feed products, medicaments and dietary supplements.

Further contemplated by the invention is the composition for use in preventing and/or curing and/or treating diarrhoea.

It was found that the sterol and/or pentacyclotriterpene component(s) present in shea olein (olein being the liquid fraction that can be obtained by fractionation of shea oil either by solvent fractionation (e.g., by fractionation in acetone at 0° C.) or by dry fractionation) or in concentrates thereof are very suitable as the active components. Concentrates and methods for their production are disclosed in EP-A-1001007, the contents of which are incorporated herein by reference. However, the active component also can be derivatives of these phytosterols or pentacyclotriterpenes The most practical components being the phytosterols and/or pentacyclotriterpenes that have the natural composition of the shea sterols or shea pentacyclotriterpenes as present in shea olein. These components can comprise more than 50 wt % of 4,4-dimethylsterols or 4,4-dimethyl pentacyclotriterpenes selected from the group consisting of alpha-amyrin, beta-amyrin, butyrospermol and lupeol. The sterols can however also be applied as free hydroxysterols (i.e. the acid groups such as acetic acid or cinnamic acid or furnaric acid which are attached to the sterols in shea have been removed therefrom e.g. by hydrolysis) or as fatty acid esters thereof (obtained by introduction of a fatty acid residue in the 2 position of the sterol or triterpene).

The effective amount can be determined by experimentation but in general this amount will be 0.005 to 30 gran/kg (e.g., 0.5 to 30 gram/kg), more preferably 0.005 to 5 gram/kg body weight of the mammal per day.

The active components can also be applied for the preparation of a food or a feed with the desired health property. Therefore, part of the invention is also a method for the preparation of a food or a feed product comprising carbohydrates and proteins wherein the food or feed product has anti-diarrhoea properties by the incorporation of an effective amount of phytosterols and/or pentacyclotriterpenes derived from the sterols or triterpenes as present in shea oil as active component. The food or feed preferably comprises 0.001 to 85 wt % of the active component, such as 0.01 to 50 wt %, even more preferably 0.001 to 4 wt %, for example 0.01 to 4 wt %. A preference exists for the use of the natural components of shea olein i.e. the natural shea sterols, or shea pentacyclotriterpenes. In particular the active component will comprise at least 50 wt % of 4,4-dimethyl derivatives of Shea sterols and/or of Shea pentacyclotriterpenes selected from the group consisting of alpha-amyrin, beta-amyrin, butyrospermol and lupeol.

As a last embodiment of our invention we found novel animal feed comprising carbohydrates and proteins (preferably in amounts of at least 1 wt % and 1 wt %, respectively, more preferably 1 to 50 wt % and 1 to 50%, respectively) and 0.001 to 4 wt % of a Shea olein comprising 2 to 12 wt % of (Shea sterols plus shea pentacyclotriterpenes) or of a concentrate of Shea sterols and/or Shea pentacyclotritetpenes comprising in total 12.5 to 80 wt % of these components. The animal feed may optionally comprise one or more vitamins and/or one or more minerals (eg, iron, calcium and zinc) and/or one or more amino acids. Other preferred components of the animal feed include: cereals, including barley, wheat, maize and mixtures thereof; soy meal, preferably solvent extracted; toasted soy beans; linseed; sunflower meal, preferably solvent extracted; whey powder; and soy bean oil. The animal feed preferably takes the form of a liquid, a powder or pellets, with pellets being more particularly preferred.

The invention will now be described with reference to the following non-limiting examples. In the examples and throughout this specification, all parts, percentages and ratios are by weight unless indicated otherwise.

EXAMPLES

Purpose

Evaluate the effect of supplementation with shea sterols on growth and post-weaning diarrhoea of growing piglets.

The weaning of piglets is a very stressful event for these animals.

One day before the start of the experiment the pigs are weighed. The piglets are distributed over the different treatment groups with the aim to establish group equality in weight, sex. Piglets smaller than 5 kg or piglets with physical disturbances are excluded from the study.

At a mean age of 27 days the pigs are weaned and randomly assigned to the 3 experimental groups and are then treated for 35 days. Pigs are fed ad libitum. The first 14 days post weaning the pigs are fed a prestarter diet. Subsequently, the piglets are changed in a period of 3 days to a starter diet. Throughout the 35 day study period the food is supplemented with either:

1. without antimicrobial growth enhancers
2. with antimicrobial growth enhancers (AMGE: 40 ppm avilamycine)
3. with shea oleine (0.4%)

The shea oleine contained 8 wt % sterols and pentacyclic terpenes. The shea oleine was obtained by fractionation of the extract from shea nuts into a stearine and oleine fraction, followed by partial bleaching and deodorising.

Piglets were weighed at the start of the experiment, at 14 days and at day 34.

Results

| Growth figures | | | |
|---|---|---|---|
| | no AMGB | AMGB | Shea extr. |
| n= | 220 | 220 | 190 |
| from weaning till 14 days post weaning | | | |
| weight at weaning (kg) | 7.7 | 7.7 | 7.7 |
| growth rate (g/day) | 193 | 185 | 190 |
| food intake (kg/day) | 0.25 | 0.23 | 0.25 p < 0.001 |
| food conversion | 1.31 | 1.28 | 1.33 |
| EW-intake per day | 0.28 | 0.26 | 0.28 p < 0.001 |
| EW-conversion | 1.47 | 1.43 | 1.49 |
| from day 15 till day 34 | | | |
| weight (kg) | 10.7 | 10.5 | 10.5 |
| growth rate (g/day) | 460 | 468 | 456 |
| food intake (kg/day) | 0.72 | 0.72 | 0.72 |
| food conversion | 1.56 | 1.55 | 1.57 |
| EW-intake per day | 0.79 | 0.79 | 0.79 |
| EW-conversion | 1.72 | 1.70 | 1.73 |
| from day 1 till day 34 | | | |
| Weight (kg) | 20.8 | 20.9 | 20.5 |
| growth rate (g/day) | 351 | 352 | 347 |
| food intake (kg/day) | 0.53 | 0.52 | 0.52 |
| food conversion | 1.51 | 1.49 | 1.51 |
| EW-intake per day | 0.58 | 0.57 | 0.58 |
| EW-conversion | 1.66 | 1.64 | 1.67 |

The food intake of the piglets until 14 days post-weaning treated without AMGB's or with shea is increased compared to piglets on a diet supplemented with AMGB's.

| Incidence of diarrhoea (%) | | | |
|---|---|---|---|
| | no AMGB | AMGB | Shea extr. |
| First week post-weaning | | | |
| no diarrhoea | 80.6 | 81.2 | 80.8 |
| past* diarrhoea | 17.1 | 17.6 | 16.0 |
| watery diarrhoea | 2.3 | 1.2 | 3.2 |
| Second week post-weaning | | | |
| no diarrhoea | 87.5 | 90.3 | 91.2 p < 0.1 |
| past diarrhoea | 12.5 | 9.5 | 8.8 |
| watery diarrhoea | 0.0 | 0.2 | 0.0 |

| -continued | | | |
|---|---|---|---|
| Incidence of diarrhoea (%) | | | |
| | no AMGB | AMGB | Shea extr. |
| Third week post-weaning | | | |
| no diarrhoea | 90.3 | 90.5 | 94.8 p < 0.01 |
| past diarrhoea | 9.4 | 9.0 | 5 |
| watery diarrhoea | 0.3 | 0.5 | 0.2 |
| number of animals required treatment | 26 | 23 | 10 |

*paste-like

In the second week post-weaning the shea treated animals display trend towards a reduced incidence of diarrhoea which reaches significance in week 3.

In conclusion, The shea extract reduces the incidence of diarrhoea significantly in the third week post-weaning. Growth of the animals was similar in all groups. The number of animals that required veterinary treatment during the study was lowest in the shea treated animals (not significant).

Example 2

Anti Diarrhoea Effect of Shea Olein

The human large gut contains a large variety of bacterial genera, species, and strains which are either beneficial (e.g., Bifidobacterium, Eubacterium and Lactobacillus) or detrimental (e.g., Clostridium, Shigella and Veillonella) to the host's health. In this context, prebiotics are defined as a "non-digestable food ingredient that beneficially affects the host by selectively stimulating the growth and/or the activity of one or a limited number of bacteria in the colon". The major products of prebiotic metabolism are Short Chain Fatty Acids (SCEAs).

An increased production of SCFAs will:

Decrease the pH in the gut which can suppress the growth of pathogenic (diarrhoea causing) bacteria Diminish fluid loss in the gut and thereby speed up remission from diarrhoea.

Provide a metabolic substrate for colonocytes but beyond that promote a normal phenotype. These effects together are supporting a healthy gut which can be expected to provide resistance against diarrhoea.

A dynamic in vitro gastrointestinal model in which the successive conditions in the lumen of the gastrointestinal tract can be simulated in an accurate and reproducible manner was used to compare different ingested products under identical and standardised conditions. In a model comprising the large intestinal (colon) compartments, the following standardised conditions are simulated: body temperature, pH in the lumen, composition and rate of secretion, delivery of a pre-digested substrate from the 'ileum', mixing and transport of the intestinal contents, absorption of water, complex, high density, metabolic active, anaerobic microbiota of human (or animal) origin, and absorption of metabolic products via a semipermeable membrane inside the colon model. This model has been validated for the production of metabolites, such as short chain fatty acids (including iso-form), gases, ammonia, and phenol compounds and used for studies on bioconversion of glucosinolates by the human colon microbiota.

The aim of these experiments was to investigate the effect of the shea oil extract containing sterol-like compounds (e.g.

tri-terpenes) on the microbiota in the TNO (Netherlands Organisation for Applied Scientific Research) in vitro model of the large intestine, with respect to activity of the microbiota. Therefore, the production of SCFAs were analyzed after feeding of the test-products. The model was inoculated with a standardized active intestinal microbiota originating from healthy adults. The standardized microbiota originated from pooled fresh stools from 10 individuals, which was cultivated in a batch fed fermentor simulating the 'caecum' conditions with storage of faecal samples in liquid nitrogen. In the ecological study, the composition of the colon microbiota was followed in time after intake of the test compounds during several days at a frequent interval. Changes in the speed of fermentation at the beginning and at the end of the long-term study indicated the adaptation or selection of the microbiota to the substrate. Analysis of the SCFAs indicated the balance between health-promoting and toxic products produced by the microbiota after addition of the shea oleine. This was compared to a control containing a similar amount of glycerides with addition of olive oil.

Shea oleine was used as a concentrate containing 35 wt % of total sterols and pentacyclic triterpenes. 400 kg of semi-refined shea oleine was deodorised and treated with a lipase in water substantially as described in EP-A-1001007-20 wt % water was added to the oleine, the mixture was stirred and treated with a combination of 0.03 wt % Lipase AY and 0.02 wt % Lipase 0. After 20 hours, the enzyme was deactivated by heating and the hydrolysed oil was washed twice with water at 80 to 90° C. The oil was dried under vacuum, filtered and distilled at 175 to 185° C. to remove fatty acids.

The results are shown in FIGS. 1 and 2.

Figure 1:
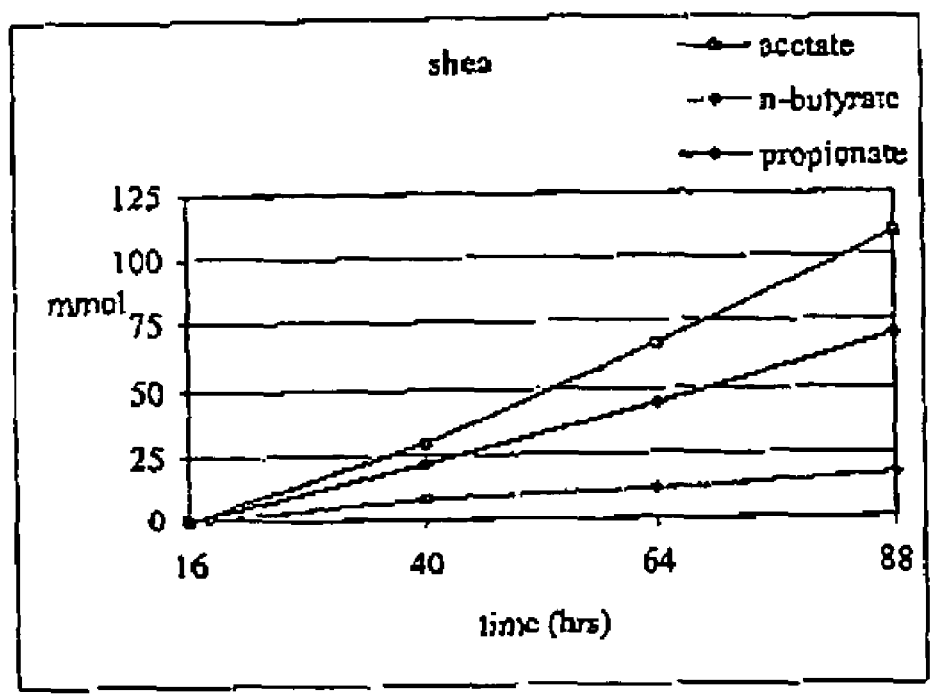
FIG. 1 is a plot of the amount of SCFAs (acetate, n-butyrate and propionate) in mmol against time for Shea olein.
Figure 2:
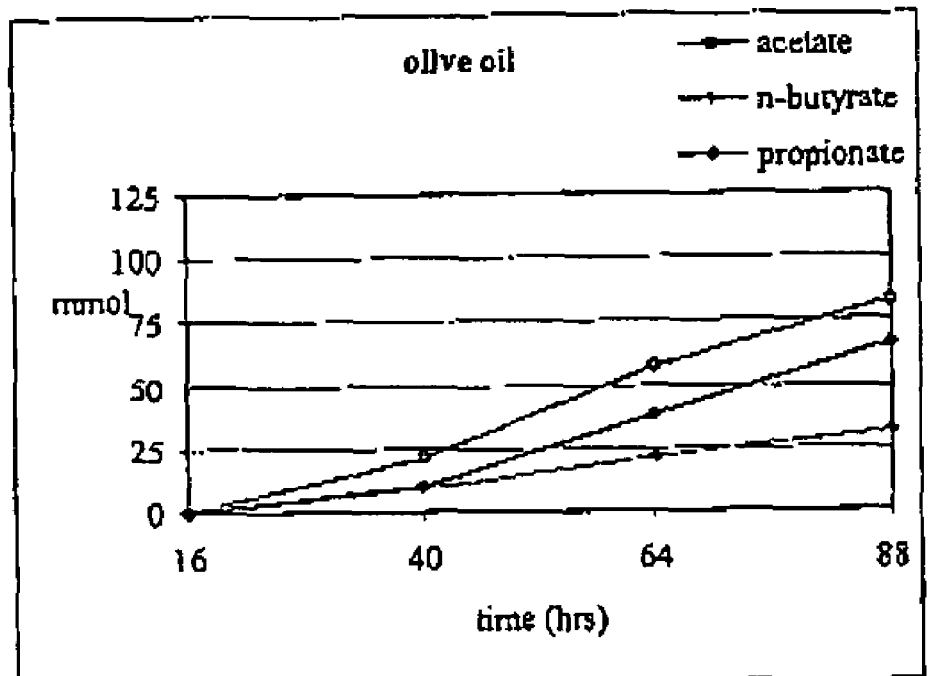
FIG. 2 is a plot corresponding to FIG. 1 but using olive oil instead of shea olein.

From the results shown in FIGS. 1 and 2, it is clear that incubation of shea olein stimulates the production of SCFAs especially acetate. This increased production of acetate can provide anti diarrhoea effects via the mechanisms as described above.

Example 3

The following is an animal feed composition of the invention suitable for weaning diets for pigs. The amounts given are in g/kg based on the weight of the composition.

| Shea extract | 5 |
| Barley | 356 |
| Soy meal solvent extracted | 85 |
| Maize, heat treated | 250 |
| Soy beans toasted | 75 |
| Linseed | 20 |
| Sunflower meal solvent extracted | 20 |
| Whey powder | 111 |
| Soy bean oil | 13 |
| Synthetic amino acids | 37 |
| Vitamins + minerals | 28 |

Example 4

The following is an animal feed composition of the invention suitable for grower diets for pigs. The amounts given are in g/kg based on the weight of the composition.

| Shea extract | 5 |
| Barley | 424 |
| Soy meal solvent extracted | 125 |
| Wheat | 200 |
| Maize, heat treated | 50 |
| Soy beans toasted | 5 |
| Linseed | 10 |
| Sunflower meal solvent extracted | 30 |
| Whey powder | 56 |
| Soy bean oil | 28 |
| Synthetic amino acids | 34 |
| Vitamins + minerals | 33 |

The invention claimed is:

1. Method for treating diarrhoea in mammals which comprises administering to the mammals an effective daily amount of a composition comprising, as active component, phytosterols and/or pentacyclotriterpenes as present in or derived from Shea oil.

2. Method according to claim 1 wherein the mammals are weaning piglets or weaning babies.

3. Method according to claim 1 wherein the phytosterols and/or pentacyclotriterpenes have a composition corresponding with the shea sterols or shea pentacyclotriterpenes as present in shea olein.

4. Method according to claim 3 wherein the shea sterols or pentacyclotriterpenes comprise more than 50 wt % of 4,4-dimethylsterols or 4,4-dimethyl pentacyclotriterpenes selected from the group consisting of alpha-amyrin, beta-amyrin, butyrospermol and lupeol.

5. Method according to claim 1 wherein the phytosterols are hydroxysterols.

6. Method according to claim 1 wherein the effective amount is 0.005 to 5 grams/kg body weight of mammal per day.

7. Method according to claim 1 wherein the active phytosterols and/or pentacyclotriterpenes are administered as part of the food or feed for the mammal.

8. Method according to claim 7 wherein the food or the feed contains 0.001 to 85 wt % of the active component.

9. Method according to claim 1, wherein the composition is selected from the group consisting of feed products, medicaments and dietary supplements.

10. Method according to claim 1 which the diarrhoea is caused by bacterial infection.

11. The method of claim 1 wherein the mammals are weaning mammals.

12. Method for the preparation of an animal feed having anti-diarrhoea or anti-scouring properties comprising incorporating in an animal feed comprising carbohydrates and proteins an effective amount of shea sterols and/or shea pentacyclotriterpenes as present in Shea oil as active component sufficient to provide said properties in said animal feed, said shea sterols and/or shea pentacyclotriterpenes comprising at least 50 wt % of 4,4-dimethyl derivatives of shea sterols and/or shea pentacyclotriterpenes selected from the group consisting of alpha-amyrin, beta-amyrin, butyrospermol and luperol.

* * * * *